US006296768B1

(12) United States Patent
Ng et al.

(10) Patent No.: US 6,296,768 B1
(45) Date of Patent: Oct. 2, 2001

(54) SEPARATING MATERIALS FOR CHROMATOGRAPHY AND ELECTROPHORESIS APPLICATIONS COMPRISING REGIODEFINED FUNCTIONALISED CYCLODEXTRINS CHEMICALLY BONDED TO A SUPPORT VIA URETHANE FUNCTIONALITIES

(75) Inventors: Siu Choon Ng; Lifong Zhang; Chi Bun Ching, all of Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 09/442,266

(22) Filed: Nov. 18, 1999

Related U.S. Application Data

(62) Division of application No. 09/140,743, filed on Aug. 26, 1998, now Pat. No. 6,017,458.

(30) Foreign Application Priority Data

Aug. 27, 1997 (SG) .................................................. 9703059

(51) Int. Cl.[7] .................................................. B01D 15/08
(52) U.S. Cl. .................. 210/635; 210/656; 210/198.2; 210/502.1; 204/601; 204/605; 204/606
(58) Field of Search ..................... 210/635, 656, 210/198.2, 502.1; 502/404; 536/103; 204/600, 601, 605, 606

(56) References Cited

U.S. PATENT DOCUMENTS

| 4,539,399 | 9/1985 | Armstrong | 210/502.1 |
| 4,867,884 | 9/1989 | Rendleman | 210/635 |
| 5,104,547 | 4/1992 | Cabrera et al. | 210/656 |
| 5,198,429 | 3/1993 | Konig | 210/635 |
| 5,294,341 | 3/1994 | Fukazawa | 210/635 |
| 5,639,824 | 6/1997 | Okamoto | 210/656 |

OTHER PUBLICATIONS

Hinze et al., *Cyclodextrins in Chromatography*, pp. 159–227 (1982).
Kawaguchi et al., *Anal. Chem.*, vol. 55, pp. 1852–1857 (1983).
Armstrong et al., *Anal. Chem.*, vol. 57, pp. 234–237 (1985).
Li et al., *Chem. Rev.*, vol. 92, pp. 1457–1470 (1992).
Allenmark, *Chromatographic Enantioseparation: Methods and Applications*, Second Edition, pp. 110–113 (1991).
Armstrong et al., *Anal. Chem.*, vol. 62, pp. 1610–1615 (1990).
Hargitai et al., *Journal of Chromatography*, vol. 628, pp. 11–22 (1993).
Hargitai et al., *Journal of Liquid Chromatography*, 16(4), pp. 843–858 (1993).
Wenz, *Angew. Chem. Int. Ed. Engl.*, vol. 33, pp. 803–822 (1994).
Oi, *Journal of Chromatography*, vol. 257, pp. 111–117 (1983).
Pirkle et al., *Journal of Chromatography*, vol. 322, pp. 295–307 (1985).
Pirkle et al., *Journal of Liquid Chromatography*, vol. 9(2&3), pp. 443–453 (1986).
Welch, *Journal of ChromatographyA*, vol. 666, pp. 3–26 (1994).
Dyas et al., *Recent Advances in Chiral Separations*, pp. 31–37 (1991).
Pirkle et al., *J. Am. Chem. Soc.*, vol. III, pp. 9222–9223 (1989).

*Primary Examiner*—Ernest G. Therkorn

(57) ABSTRACT

Novel and improved chiral stationary phases (CSP) materials comprising a support and completely regiodefined derivitised cyclodextrin chemically bonded via single or double urethane linkage(s) universally applicable in HPLC, LC, TLC, and CCE are obtained using a process based on the almost quantitative reaction of pre-synthesized regiodefined per-functionalized mono- or di- azidocyclodextrin with primary amines.

5 Claims, 3 Drawing Sheets

R= ALKYL, ARYL, ESTER OR CARBAMATE

R= ALKYL, ARYL, ESTER OR CARBAMATE

A: AMINIZED SILICA GEL  B: PRODUCT OF EXAMPLE 2
C: PRODUCT OF EXAMPLE 1  D: PRODUCT OF EXAMPLE 3

SEPARATING MATERIALS FOR CHROMATOGRAPHY AND ELECTROPHORESIS APPLICATIONS COMPRISING REGIODEFINED FUNCTIONALISED CYCLODEXTRINS CHEMICALLY BONDED TO A SUPPORT VIA URETHANE FUNCTIONALITIES

This application is a divisional of application Ser. No. 09/140,743, filed on Aug. 26, 1998, now U.S. Pat. No. 6,017,458, the entire contents of which are hereby incorporated by reference.

FIELD OF THE INVENTION

The present invention relates to the development of novel separating materials for high performance liquid chromatography (HPLC), liquid chromatography (LC), thin layer chromatography (TLC), capillary electrophoretic chromatography (CCE) and counter-current chromatographic processes, which essentially comprise amine-bearing support materials and functionalised cyclodextrins (CD) chemically bonded via a urethane linkage. More significantly, our procedure affords materials in which the cyclodextrins are bonded to the support with well defined chemical structure and good experimental reproducibility.

BACKGROUND OF THE INVENTION

The applicability of cyclodextrins in chromatographic separation and purification processes were previously described at length in reviews by W. L. Hinze, *Separation and Purification Methods*, 1981, 10(2), 159–237; Y. Kawaguchi, et al., *Anal. Chem.*, 1983, 55, 1852; D. M. Armstrong, et al., *Anal. Chem.*, 1985, 57, 234 and S. Li, et al., *Chem. Rev.*, 1992, 92, 1457. Chromatographic separation on chiral stationary phases (CSP) is also the most convenient analytical method for the determination of enantiomeric purity (see for example S. G. Allenmark, *Chromatographic Enantioseparations: Methods and Applications*, 2nd ed., Prentice Hall, N.J., 1991). In recent years, tremendous research efforts were made in bonding cyclodextrins to solid matrices, such as silica gel, via amino or amido linkages. However, these bonds were inherently unstable to hydrolysis, thus placing severe limitations on their use in aqueous media. Alternative approaches for immobilizing CD using hydrolytically more stable ether linkages (U.S. Pat. No. 4,539,399) or carbamic acid moieties (U.S. Pat. No. 503,898) were also investigated. However, in all these approaches, arising from the presence of multiple hydroxy moieties in the CD starting materials, regioselective derivatisation of cyclodextrin cannot be readily effected. Thus, reaction may take place on the 2, 3 or 6- position of cyclodextrin and may result in mixtures of multi-functionalised CDs instead of the desired regiodefined compound.

It was often reported that derivatized CD stationary phases show definite enantioselectivity for a variety of compounds while pristine cyclodextrin bonded LC stationary phases depict low enantioselectivity. Thus, as an example, enantioselectivity of the materials were generally increased with increasing degree of derivatisation of the —OH groups on CD with carbamate groups on cyclodextrin as of an increasing surface concentration of the functionalised cyclodextrin immobilized on the support materials (D. W. Armstrong et al., *Anal Chem.*, 1990, 62, 1610; T. Hargitai et al., *J. Chromatogr.*, 1993, 628, 11; T. Hargitai, et al., *J. Liq. Chromatogr.*, 1993, 16(4), 843). In order to maximise the extent of cyclodextrin derivatisation, large molar excesses of derivatizing reagents under vigorous conditions were often used. However, as the derivatisation processes invariably involved the prior immobilization of underivatised cyclodextrin on the support material followed by functionalisation procedures involving solid-liquid phases, partial derivatisation of the hydroxyl groups of the cyclodextrin usually resulted with large, sterically encumbered substituents consistently having a lower extent of derivitisation. In addition, these methods did not give good reproducibility or uniformity of product with the consequence that separation of enantiomers may vary from batch to batch of the obtained CD-based CSP.

OBJECTIVES AND BRIEF SUMMARY OF THE INVENTION

One objective of this invention is the obtainment of novel and improved CSP materials comprising a support and completely regiodefined derivatised cyclodextrin chemically bonded via single or double urethane linkage(s), universally applicable in HPLC, LC, TLC and CCE. Application in counter-current chromatographic processes would thus afford a viable and efficient means into bulk/ industrial scale enantioseparation, which would be of interest particularly to pharmaceutical firms involved in enantioseparation of racemic chiral drugs.

Another objective of the invention is to derive methodologies for the preparation of materials mentioned above. These and other objectives will become apparent or will be highlighted in the ensuing description.

The present invention is based on the almost quantitative reaction of pre-synthesized regiodefined perfunctionalized monoazidocyclodextrin with primary amines based on an extended application of the Staudinger reaction which we have investigated. In addition, application of existing synthetic strategies (G. Wenz, *Angew. Chem. Int. Ed. Eng.*, 1994, 33, 803 and references therein) into regiodefined disulphonated CDs, often referred to as capped cyclodextrins, can likewise afford regiodefined diazido perfunctionalised CDs suitable for reaction with amines. When aminized silica gel was used in place of the primary amine under similar conditions, the perfunctionalized mono- (or di-)azidocyclodextrin could be immobilized onto the surface of silica gel easily via stable urethane linkage(s), usually adopted in Pirkle-typed or protein-based CSPs (N.Oi, et al., *J. Chromatogr.*, 1983, 111, 257; W. H. Pirkle, *J. Chromatogr.*, 1985, 322, 295; W. H. Pirkle, *J. Liq. Chromatogr.*, 1986, 9, 443; C. J. Welch, *J. Chromatogr.* A, 1994, 666, 3; W. H. Pirkle, et al., *J. Am. Chem. Soc.*, 1989, 111, 9222; A. M. Dyas, *Recent Advances in Chiral Separations*, Plenum Press, New York, 1991). Furthermore, when perfunctionalized mono- or diazidocyclodextrins are reduced into the corresponding perfunctionalized mono- or diamino cyclodextrins, the latter can be easily anchored onto the surface of the support by suitable coupling reagents via urethane or amido linkages.

The invention therefore relates to a separating material used in chromatography, essentially comprising a support material and regiodefined perfunctionalized cyclodextrins chemically bonded to this support and characterized by a bonding via single or double urethane moieties. The invention also relates to a process for the production of this separating material in which the perfunctionalized mono-(or di)azidocyclodextrin is:

a. coupled directly to any support which is carrying free —NH$_2$ groups on the surface of the support.

b. reacted with any alkenyl amines to give the corresponding perfunctionalized cyclodextrin with mono- (or di)alkenyl substituted side chain(s) via urethane linkage(s) and then allowing this derivative to be hydrosilylized with $HSiR_nX_{3-n}$ (where R and X are alkyl, alkyloxy, aryl or halide) and thereafter effecting an immobilization onto the surface of a support material.

c. reacted with any aminosilanes containing at least one further reactive group to afford the corresponding cyclodextrin-silane derivative. The resulting cyclodextrin-silane derivative is treated with silica gel to afford the perfunctionalized cyclodextrin bonded silica gel.

d. reduced to perfunctionalized mono- or diaminocyclodextrin and then anchored onto the surface of a support via coupling reagents.

Support which can be employed are silica gel or any alternative inorganic materials such as $Al_2O_3$, $TiO_2$ or $ZiO_2$ or synthetic polymer supports, preferably incorporating existing free $NH_2$ group on the surface. The support employed of choice is silica gel, which is commercially available in a wide range of different shapes and sizes.

DETAILED DESCRIPTION OF THE INVENTION

Figure 1:
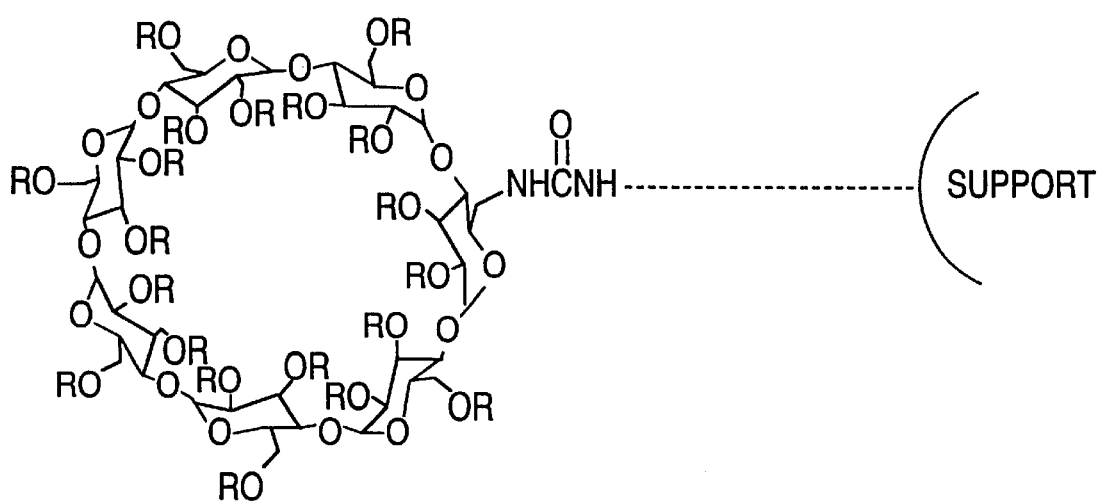
FIG. 1 depicts a representative completely substituted cyclodextrin (β-cyclodextrin) immobilized onto the surface of a support by a urethane linkage.
Figure 2:
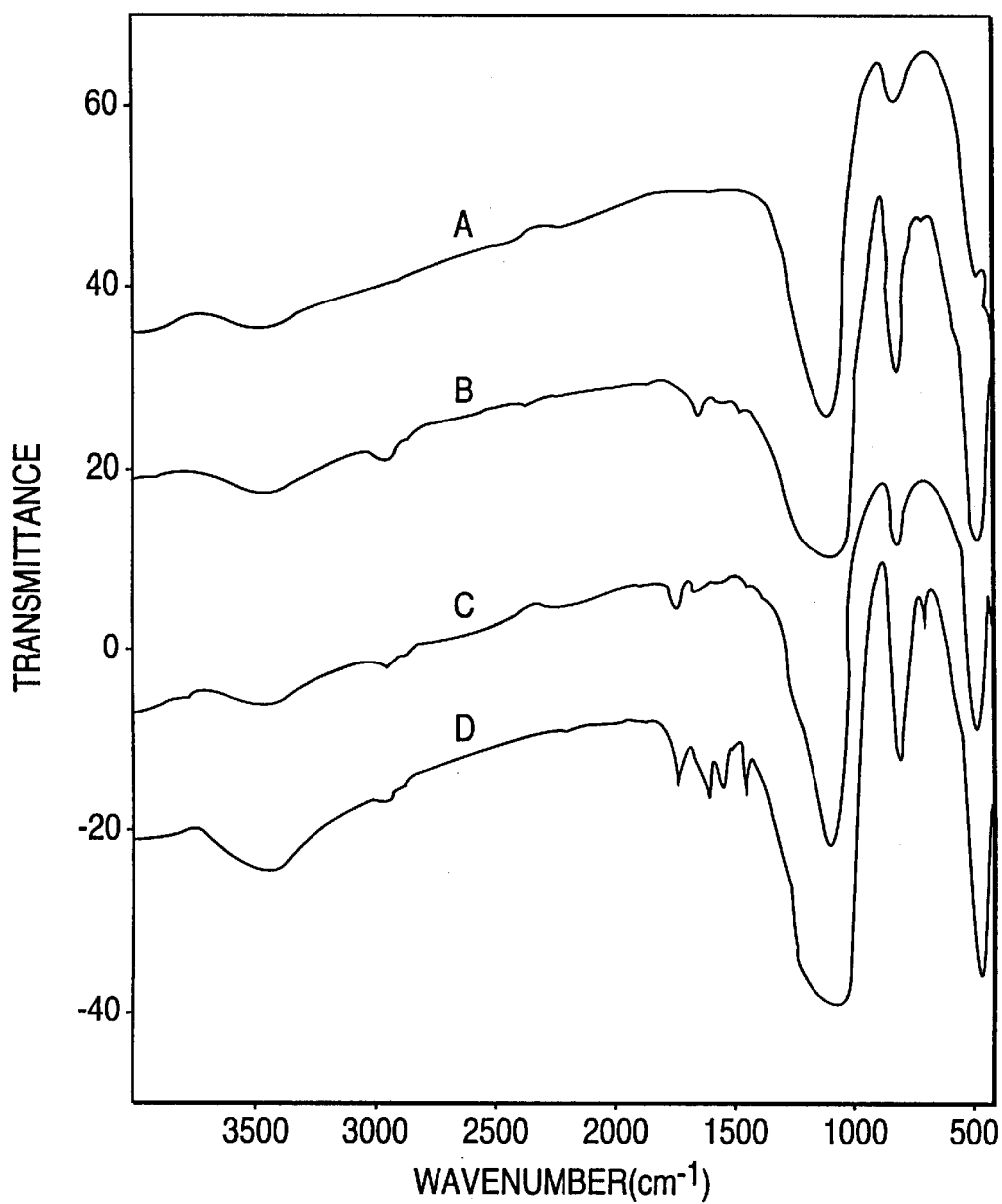
FIG. 2 depicts the FT-IR spectra of the materials obtained by present invention with different substituted group, which prove that the perfunctionalized cyclodextrins have already been anchored to the surface of the silica gel.
Figure 3A:
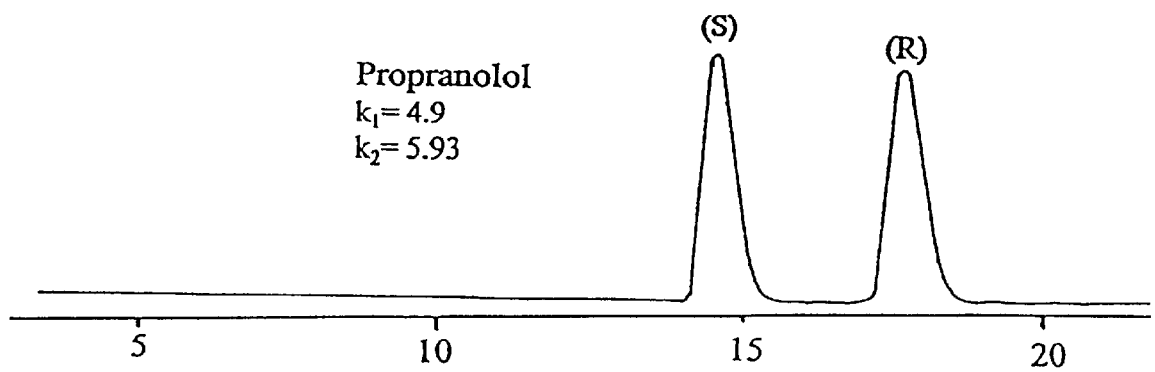
FIGS. 3A, 3B, and 3C depict the representative HPLC enantioseparation of racemic β-blockers propranolol, oxprenolol, and alprenolol using the product of example 3.
Figure 3B:
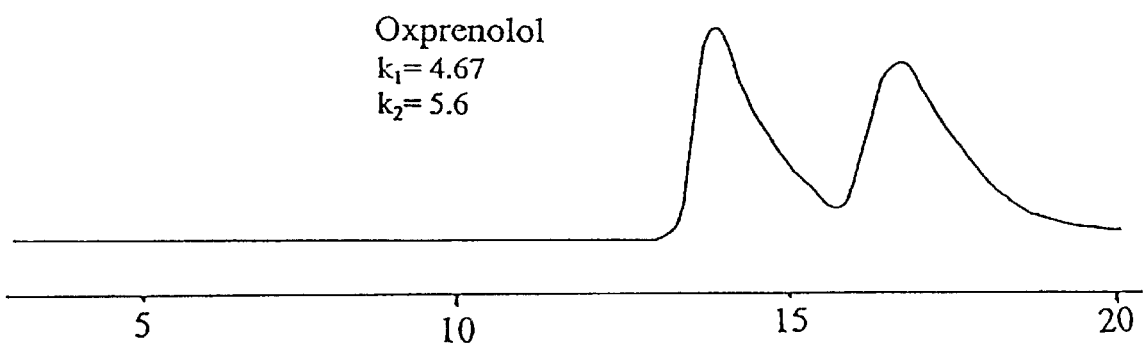
Figure 3C:
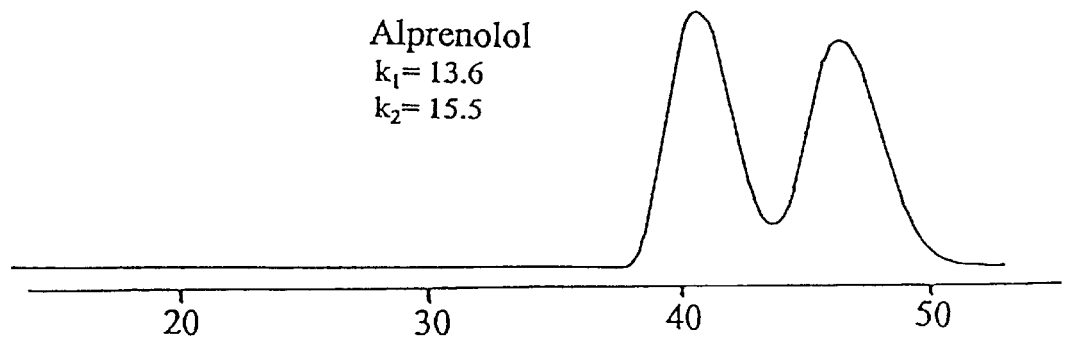

The CSP according to the invention can be produced by four different approaches as in a. to d. above. From a. to c., the key step in all variety is the same, involving reacting perfunctionalized mono- (or di)azidocyclodextrin with free amines via a facile one-pot procedure in high yield or good immobilization contents. The cyclodextrin used may be of any of the α, β or γ form or combination thereof whilst the derivatisation substituent groups may be alkyl, aryl, ester and carbamate.

In method a., the perfunctionalized mono- (or di-) azidocyclodextrin is coupled directly onto a support which has already been modified with amino groups. This —$NH_2$ bearing material can either be obtained commercially in finished form or prepared by a silylation reaction of the support with an appropriate aminosilane. For this purpose, particular preference is made to aminosilane such as, for example, 3-aminopropyltrimethoxysilane, 3-aminopropyltriethoxysilane, 3-(2-aminoethyl) aminopropyltriethoxysilane and 3-(2-aminoethyl) aminopropyltrimethoxy silane.

In the method b., suitable alkenyl amines may be, but not limited to the form: $CH_2=CH(R_1)_m(R_2)_nNH_2$ where m, n=1–20.

In the method c., the aminosilanes described in method a. are suitable for this purpose. Here too, urethane linkage(s) is formed between the $NH_2$ groups of the support and the perfunctionalized cyclodextrin.

In the method d., the coupling reagents may be OCN—R—NCO, ClOC—R—COCl or $SiX_nY_{3-n}$—R—NCO, where X and Y are alkyl, alkyloxy, aryl or halide.

The connecting spacer between the support and the perfunctionalized cyclodextrin may comprise a relative short or relative long chain. This chain preferably has 3–20 atoms and may contain nitrogen, oxygen or silicon atoms in addition to carbon atoms.

The material obtained according to the invention can, if desired be further subjected to an "end-capping" reaction. In this, the remaining hydroxyl groups on the silica gel surface are reacted in a known manner with a reactive silane, such as, for example, trimethylchlorosilane or alternatively hexamethyldisilazane, in order to comnplete the blocking of the surface hydroxyl groups.

Above all, by present invention, the derivatised cyclodextrin can be immobilized onto the surface of the support via a single (or double) urethane linkage(s). In the CSP material obtained by the present invention, the chemical structure of cyclodextrin is well defined and the immobilisation can be effected with good reproducibility.

EXAMPLES

The following examples illustrate the practice of the present invention.

Cyclodextrin monofunctionalized with an azido moiety at the 6-position was prepared using the previously reported procedure by L. D. Melton et al., *Carbohydr. Res.*, 1971, 18, 29; H. Parrot-lopez, et al, *Tetrahedron Lett.*, 1992, 33, 209; R. C. Petter, *J. Am. Chem. Soc.*, 1990, 112, 3860. Cyclodextrin difunctionalized with azido moieties at the 6-position was prepared according to the reported method by I. Tabushi, et al., Tetrahedron Lett., 1977, 18, 1527; I. Tabushi, et al., J. Am. Chem. Soc., 1984, 106, 5267; G. L. Yi, et al., *J. Org. Chem.,* 1993, 58, 2561. The other hydroxyl groups of the 6-mono (or di-)azido substituted cyclodextrin can subsequently be completely derivatised with different substituents groups such as alkyl, aryl, ester and carbamate.

Peracetylated-monoazido-β-cyclodextrin was prepared easily by stirring 6-monoazido-β-cyclodextrin with $(AcO)_2O$/Pyridine at 40° C. in 90% yield.

Pernethylated-monoazido-β-cyclodextrin was prepared by reaction of 6-monoazido-β-cyclodextrin in $CH_3I$/DMF/NaH at 40° C. in 70% yield.

Monoazido-β-cyclodextrin perphenylcarbamate was prepared by reaction of 6-monoazido-β-cyclodextrin in PhNCO/Pyridine at 80° C. in 70% yield.

Aminized silica-gel was prepared according to the literature method by T. Hargital et al., *J. chromatogr.*, 1993, 628, 11, with the following composition as determined from elemental analysis: C% 3.25, H% 0.96, N% 0.98.

Example 1

4 g of animized silica gel was stirred in 30 ml ahydrous THF into which a continuous stream of $CO_2$ gas was passed. After 20 mins, 1.2 g of peracetylated monoazido-β-cyclodextrin in 10 ml anhydrous THF was added. Stirring was continued another 5 mins, whence 0.3 g of triphenylphosphine in 10 ml anhydrous THF was added. The mixture was stirred 10 hrs with constant bubbling of $CO_2$ at room temperature. The reaction mixture was then transferred to a soxhlet extraction apparatus and extracted with acetone for 24 hrs. After removal of the acetone in vacuo, the peracetylated cyclodextrin immobilized silica gel was obtained having the following composition as determined from elemental analysis: C% 8.89, H% 1.78, N% 0.80.

Examples 2 and 3

Example 1 was repeated using monoazide-permethyl-β-cyclodextrin or monoazido-β-cyclodextrin perphenylcarbamate in place of the peracetylated monoazido-β-cyclodextrin of example 1. The elemental analyses were as follow:
1. Bonded with permethylated-β-cyclodextrin: C% 8.82, H% 1.88, N% 0.94.
2. Bonded with β-cyclodextrin perphenylcarbamate: C% 11.32, H% 2.0, N% 1.24.

Example 4

A solution of the 10-undecenylamine (2.0 mmol) in 10 ml dry THF was saturated with dry $CO_2$ at room temperature with stirring, immediately precipitate of ammonium carbamate derivative was observed. With continuous bubbling of $CO_2$ into the suspension, monoazide peracetyl β-cyclodextrin(1.80 mmol) in 10 ml anhydrous THF was added in a single portion, followed by addition of $PPh_3$(1.80 mmol) in 10 ml dry THF. This was allowed to react for about 5 hrs, TLC revealed that no starting materials existed. After evaporation to dryness, the product was purified by column chromatography with ethyl acetate-acetone(1:1) as eluant in 97% yield.

Mp:115–117° C., $[\alpha]$=+106.1°(c 1.0 in $CHCl_3$); IR: 3427 (N-H), 2937, 2859 (C-H), 1744, 1663 (C=O); $^1$H NMR ($CDCl_3$) δ(ppm): 5.89–5.76 (m,1H), 5.38–5.21 (m, 7H), 5.16–4.94(m, 11H), 4.84–4.68 (m,7H), 4.58–4.50 (m, 6H), 4.35–4.26 (m, 6H), 4.20–4.05 (m, 7H), 3.78–3.66 (m, 7H), 3.57–3.51 (m, 1H), 3.49–3.32 (m, 1H), 3.30–3.16 (m,1H), 3.11–3.00 (m, 1H), 2.18–2.00 (several s, 60H), 1.46–1.19 (m, 16H); $^{13}$C NMR ($CDCl_3$, 25° C.) δ (ppm):170.6–169.3, 158.0, 139.1, 113.9, 96.6–96.4, 78.3–76.2, 70.7–69.5, 62.4, 41.2, 40.3, 33.7–26.8, 20.6–20.4; Elemental analysis calcd for $C_{94}H_{132}N_2O_{55}$ (2168.76): C 52.01%, H 6.13%, N 1.29%; Found C 51.72%, H 6.30%, N 1.20%.

Examples 5 and 6

Example 4 was repeated using monoazido-permethyl-β-cyclodextrin or monoazido-β-cyclodextrin perphenylcarbamate in place of the monoazido-peracetyl-β-cyclodextrin of example 4 with basic properties shown as following:
6-(10'-undecenyl)urea-permethyl-β-cyclodextrin: yield 97%, Mp: 72–74° C. $[\alpha]$=+132.90° (c 1.0, $CHCl_3$);
6-(10'-undecenyl)urea perphenylcarbarmate-β-cyclodextrin: yield 95%, Mp: 198–200 ° C. $[\alpha]$=+8.5° (C1.0, $CHCl_3$);

Example 7

1.5 g of product obtained in Example 4 was stirred with 5 ml triethoxysilane and 10 mg of tetrakls (triphenylphosphine)platinum at 60° C. After 24 hrs the mixture was adsorbed with 2 cm high silica gel in a Buchner funnel and washed with 100 ml ether, after removal of the ether and volatile by vacuum, the residue was dissolved in 50 ml anhydrous toluene, 4.0 g of silica gel(which had already been dried over vacuum at 120° C. for) was added, the mixture was stirred at 80° C. for 8 hrs. After filtration and extracted in soxhlet apparatus with acetone for 24 hrs, the product was obtained with the element analysis as shown following:
C% 6.98, H% 1.52,N% 0.10

Examples 8 and 9

Example 7 was repeated using monoazido-permethylated-β-cyclodextrin or monoazido-β-cyclodextrin perphenylcarbamate in place of the peracetylated monoazido-β-cyclodextrin of example 7 with elemental analyses shown as following:
1. Bonded with permethylated-β-cyclodextrin: C% 6.50, H% 1.32, N% 0.10.
2. Bonded with β-cyclodextrin perphenylcarbarnate: C% 9.40, H% 1.80, N% 0.83.

It will be noted that in the products produced by the present invention, the cyclodextrin is completely derivatised with the exception of the single (or double) 6-glucosidic position(s) connected to the support material via urethane linkage(s) which is (are) very stable and frequently adopted in Pirkle-typed and Protein-based CSPs. Such complete modification of cyclodextrin affords a regiodefined chemical structure and have good experimental reproducibility.

Having now described the invention, it is not intended that it be limited except as may be required by the appended claims. The embodiments of the invention in which an exclusive property of the privilege is claimed are defined in the following claims.

What is claimed is:

1. A method for chromatographic or electrophoretic separation of a mixture comprising, respectively, contacting a sample comprising said mixture with or applying a sample comprising said mixture to a separation support material, said separation support material being one produced by a process comprising any one of the following steps:

(a) reacting a regiodefined mono-azido perfunctionalized cyclodextrin or a regiodefined di-azido perfunctionalized cyclodextrin with a support that carries free NH2 groups;

(b) reacting a regiodefined mono-azido perfunctionalized cyclodextrin or a regiodefined di-azido perfunctionalized cyclodextrinwith an alkenyl amine to produce a product comprising a C=C group linked to a side chain via a urethane linkage, further hydrosilating the C=C group of said product with an active silane, and chemically immobilizing the product onto the surface of a support;

(c) reacting a regiodefined mono-azido perfunctionalized cyclodextrin or a regiodefined di-azido perfunctionalized cyclodextrin with an aminosilane containing at least one further reactive group to form a product, and chemically immobilizing the product onto a surface of a support; and (d) reducing a regiodefined mono-azido perfunctionalized cyclodextrin or a regiodefined di-azido perfunctionalized cyclodextrin to a monoamino or diamino perfunctionalized cyclodextrin, and then anchoring the mono- or diamino perfunctionalized cyclodextrin onto the surface of a support by a coupling reagent, and, in the case of electrophoretic separation, applying an electric field.

2. The method for separation of claim 1, which comprises method for chromatographic separation of a mixture.

3. The method of claim 2, wherein said mixture comprises a mixture of enantiomers of a compound.

4. The method for separation of claim 1, which comprises method for electrophoretic separation of a mixture.

5. The method of claim 4, wherein said mixture comprises a mixture of enantiomers of a compound.

* * * * *

UNITED STATES PATENT AND TRADEMARK OFFICE
CERTIFICATE OF CORRECTION

PATENT NO.    : 6,296,768 B1
DATED         : October 2, 2001
INVENTOR(S)   : Siu Choon NG et al.

It is certified that error appears in the above-identified patent and that said Letters Patent is hereby corrected as shown below:

<u>Title page,</u>
Item [75], Inventors, please correct the spelling of the second inventor's name from "Lifong Zhang" to -- Lifeng Zhang --.

Signed and Sealed this

Twenty-seventh Day of August, 2002

*Attest:*

*Attesting Officer*

JAMES E. ROGAN
*Director of the United States Patent and Trademark Office*